United States Patent [19]

Nugent

[11] 4,417,981
[45] Nov. 29, 1983

[54] BLOOD PHASE SEPARATOR DEVICE

[75] Inventor: Edward L. Nugent, North Caldwell, N.J.

[73] Assignee: Becton, Dickinson and Company, Paramus, N.J.

[21] Appl. No.: 260,530

[22] Filed: May 4, 1981

[51] Int. Cl.³ ............................................. B01D 21/26
[52] U.S. Cl. ..................................... 210/209; 210/516;
        210/927; 494/16; 494/38; 422/73; 422/101
[58] Field of Search .................. 23/230 B; 422/73, 99,
        422/101; 210/782, 789, 209, 516, 517, 518, 927;
        233/1 A, 26

[56] References Cited

U.S. PATENT DOCUMENTS

| 3,929,646 | 12/1975 | Adler | 210/927 |
|---|---|---|---|
| 3,945,928 | 3/1976 | Ayres | 210/927 |
| 3,957,653 | 5/1976 | Blecher | 210/789 |
| 3,957,654 | 5/1976 | Ayres | 210/927 |
| 3,976,579 | 8/1976 | Bennett | 210/927 |
| 3,981,804 | 9/1976 | Gigliello | 210/927 |
| 4,055,501 | 10/1977 | Cornell | 210/927 |
| 4,088,582 | 5/1978 | Murty | 210/789 |
| 4,101,422 | 7/1978 | Lamont | 210/927 |
| 4,189,382 | 2/1980 | Zine | 210/927 |
| 4,202,769 | 5/1980 | Greenspan | 210/927 |

Primary Examiner—Ernest G. Therkorn

[57] ABSTRACT

A blood collection device for receiving whole blood adapted to be centrifuged into phases of lighter and heavier specific gravity includes a container with proximal and distal ends and a penetrable stopper at the proximal end. A separator assembly inside the container includes a receptacle with a thixotropic barrier material therein. An aperture in the receptacle faces toward the distal end of the container. The barrier material has a specific gravity intermediate the specific gravities of the lighter and heavier phases of blood and is adapted to flow under its own influence through the aperture during centrifugation. The barrier material then travels to a position intermediate the lighter and heavier phases of blood separated during centrifugation and adheres to the inside wall of the container to form a barrier.

14 Claims, 16 Drawing Figures

BLOOD PHASE SEPARATOR DEVICE

BACKGROUND OF THE INVENTION

1. Field of the Invention

The present invention relates to a blood collection device for receiving a sample of whole blood, and more particularly, concerns such a device wherein the blood is to be centrifuged into lighter and heavier phases of specific gravity. The present invention further contemplates a separator assembly for use in a blood collection device for providing a barrier between lighter and heavier phases of blood separated by centrifugation.

2. Description of the Prior Art

In the laboratory analysis of blood collected from a patient, the different constituent phases of blood require separate analysis. Blood plasma is separated from blood cells by a standard centrifuging procedure which readily accomplishes this separation since the specific gravity of the cellular phase of blood is heavier than the plasma phase of blood. In a similar fashion, whole blood is often separated into a clotted phase and a serum phase once again by centrifuging procedures and reliance upon the differences in the specific gravities of these two phases of blood. Since the whole blood is normally collected in a test tube-type of blood collection container which is subsequently centrifuged, separation of the phases occurs in the same vessel. Thereafter, removal of the separated phases from the test tube must be accomplished cleanly so that there is no subsequent intermixing of the separated phases. Various decanting procedures, both by pouring and by manual filtration devices, have been employed in the past to collect each of the separated phases following centrifugation. These procedures must, however, be done carefully and quickly so that only one phase is collected. On the other hand, these procedures normally are done immediately after the centrifuging operation because transport to another laboratory area would cause subsequent intermixing and therefore compromise the purity of the separated phases. Thus, transport of the vessel containing separated phases after centrifugation and a longer time period after centrifugation to collect one or both separated phases are features which have been sought.

Early efforts to provide a barrier or sealant between the separated phases of whole blood are described in U.S. Pat. Nos. 3,780,935 and 3,852,194. In U.S. Pat. No. 3,780,935, the sealant is introduced after the whole blood has been collected which compromises the desirable features of a closed system. In U.S. Pat. No. 3,852,194, the sealant material is initially placed at the bottom of the blood collection container, but has a tendency to move from its initial location near the closed end of the tube toward the eventual fluid-phase interface. This movement was described as undesirable in U.S. Pat. No. 3,920,549 wherein an improvement was described. This improvement included an energizer member for maintaining the gel material in a position adjacent the container bottom and then relying upon the energizer member to control the flow of the gel material due to the forces generated against the energizer member during centrifugation.

In U.S. Pat. No. 3,957,654, a sealant barrier assembly is introduced into the blood collection container after the blood has been first centrifuged and separated into its two phases. A phase partitioning device is also disclosed in U.S. Pat. No. 4,055,501 wherein the partitioning device is disposed within the collection tube before blood is collected therein. Both U.S. Pat. Nos. 3,957,654 and 4,055,501 disclose a barrier sealant within a cylindrical vessel which includes a slidable piston element. Upon centrifugation, these pistons slide to compress the volume within the cylindrical vessel thereby forcing barrier sealant material radially outwardly through holes in the vessel whereupon the barrier sealant adheres to the inside walls of the container to provide a physical separation between the phases of blood. While these patented devices describe a technique for effectuating the barrier between the lighter and heavier phases of blood, other improvements for control of the barrier material to the interface between the phases are still being sought. It is to this end that the present invention is directed.

SUMMARY OF THE INVENTION

A blood collection device for receiving whole blood adapted to be centrifuged into a phase of lighter specific gravity and a phase of heavier specific gravity includes a container having a longitudinal axis, a proximal end and a distal end. A stopper is positioned at the proximal end penetrable by a sharp instrument for delivering blood to the container. Means is inside the container for maintaining the separation of the lighter phase from the heavier phase of blood after centrifugation. This means includes a receptacle with a barrier material therein, the barrier material being substantially non-flowable under normal gravity conditions before centrifugation. During centrifugation of the device, the barrier material is flowable. Aperture means is included in the receptacle facing toward the distal end of the container. The barrier material has a specific gravity intermediate the specific gravities of the lighter and heavier phases of blood. During centrifugation, the barrier material is adapted to flow under its own influence through the aperture, travel to a position intermediate the lighter and heavier phases separated during centrifugation and adhere to the inside wall of the container to form a barrier between the phases to maintain the separation therebetween.

In a preferred embodiment of this aspect of the present invention, the means for maintaining the separation is a separator assembly positioned inside the blood collection container intermediate the ends of the container and adapted to move along its longitudinal axis. The receptacle is positioned inside the container to provide an annular clearance between itself and the inside wall of the container for blood passage toward a closed end of the container during the blood collection procedure. Both the size of the aperture and the viscosity of the barrier material cooperate to prevent the barrier material from flowing out of the aperture under normal gravity conditions, normally 1–3g's. Each of the separator assembly (as a unit) and the receptacle alone has a specific gravity greater than the specific gravity of the heavier blood phase, with the separator assembly adapted to move toward the closed end of the container during centrifugation of the device. On the other hand, the barrier material has specific gravity intermediate the specific gravities of the lighter and heavier phases of blood and is adapted to form a barrier at the interface of the lighter and heavier phases as heretofore mentioned.

In another embodiment of the present invention, wherein the lighter and heavier phases of blood represent the serum and clotted phases, respectively, it is desirable to induce clotting so that the procedure for separating serum can be done rapidly. In this embodiment, the separator assembly includes a removable blood clotting activator on its surfaces in the path of blood flowing into the container so that whole blood contacting the activator during such passage picks up the activator to induce rapid blood clotting.

In still another embodiment of the present invention, a separator assembly is positioned inside the container substantially similar to such assembly described above. This separator assembly includes an opening in the receptacle opposite from the aperture on one side of the receptacle. The separator assembly and the barrier material in the receptacle alone each have a specific gravity intermediate the specific gravities of lighter and heavier phases of blood. During centrifugation of this embodiment, the separator assembly is adapted to move toward the closed end of the blood collection container. Due to the centrifugal forces imparted against the barrier material through the aperture facing the closed end of the container, the barrier material flows through the opening in the receptacle and travels to a position intermediate the lighter and heavier phases of blood separated during centrifugation in order to form the barrier therebetween.

In another aspect of the present invention, a separator assembly is employed within a blood collection device of the type adapted to receive a sample of whole blood and be centrifuged into phases of lighter and heavier specific gravities. This separator assembly is that which has been substantially described above.

In accordance with the principles of the present invention, the improved blood collection device and the separator assembly provide a mechanism for positive release and flow direction control of the barrier material to the interface between light and heavier phases of blood. Furthermore, one embodiment of the present invention provides positive means for releasing of a clotting activator material so that serum can be effectively separated from clotted blood. In addition, the separator assembly of the present invention is included preferably within an evacuated blood collection container before blood is collected therein so that a closed system is provided. The preferred separator assembly of the present invention does not require the movement of piston within a cylinder such as described in U.S. Pat. Nos. 3,957,654 and 4,055,501.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiments illustrated. The scope of the invention will be measured by the appended claims and their equivalents.

Figure 1:
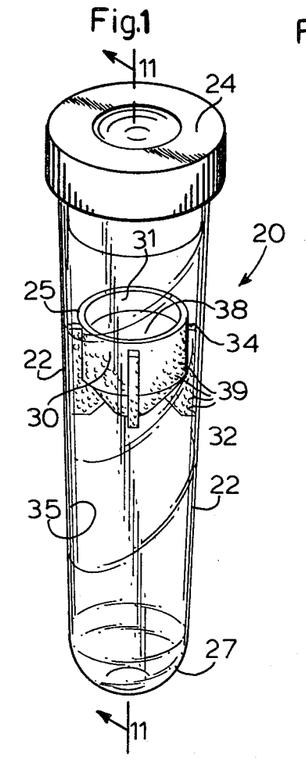
FIG. 1 is a perspective view of the preferred embodiment of a blood collection device of the present invention adapted to separate serum from clotted phases of blood.
Figure 2:
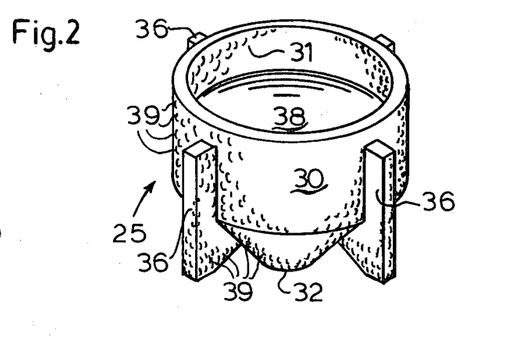
FIG. 2 is a perspective view of the preferred embodiment of the separator assembly illustrated inside the collection device in FIG. 1 and useful in separating the serum and clotted phases of blood.
Figure 3:
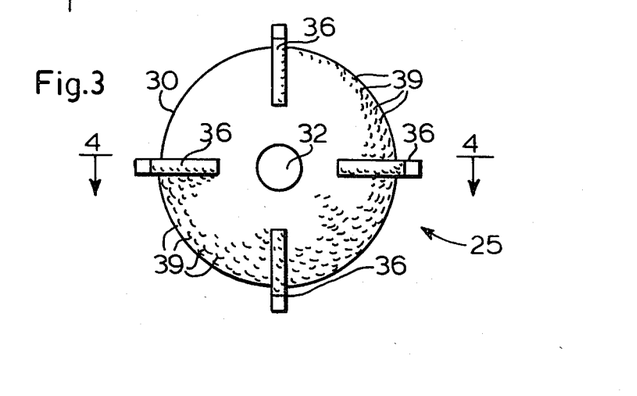
FIG. 3 is a bottom plan view of the separator assembly of FIG. 2.
Figure 4:
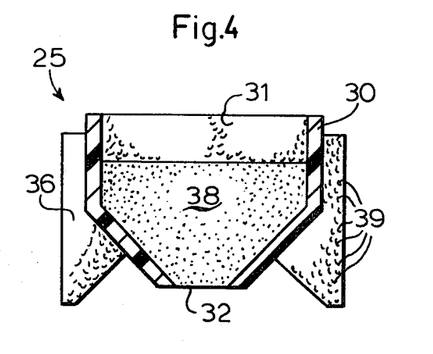
FIG. 4 is a cross-sectional view of the separator assembly taken along line 4—4 of FIG. 3.

Adverting to the drawings, and FIG. 1 in particular, there is illustrated a blood collection device 20 for receiving a sample of whole blood which is to be centrifuged into a phase of lighter specific gravity and a phase of heavier specific gravity. Blood collection device 20 includes three general components: a blood collection container 22, a penetrable stopper 24 and a separator assembly 25. Container 22 is preferably in the form of an elongate test tube, such as clear glass, plastic or the like, having a closed distal end 27 and an open proximal end 28. Container 22 is also preferably cylindrically shaped. Penetrable stopper 24 is sized to fit into open end 28 and sealingly close same. This stopper is generally penetrable by a sharp instrument such as a hollow needle 29 (seen by briefly referring to FIG. 11). This stopper is usually made from rubber, natural or synthetic, or the like elastomers. In the preferable state, the interior of container 22 is evacuated in order to provide a negative pressure gradient therein so that once the needle penetrates the stopper blood will readily flow into the container. Separator assembly 25 is positioned inside the container 22 before stopper 24 is placed in open end 28 and also before the interior of the container is evacuated. As seen in FIG. 1, separator assembly 25 is positioned at a central region within container 22 intermediate the open and closed ends of the container. Although this position is so illustrated, it is pointed out that this position is merely preferable, especially if the whole blood is to be separated into serum and clotted phases. Other positions of the separator assembly, including a position at the closed end of the container, are within the purview of the present invention, depending upon the specific gravity of the separator assembly. FIGS. 2-4, taken in conjunction with FIG. 1, illustrate the details of the preferred separator assembly of the present invention.

Separator assembly 25 includes a receptacle 30 which preferably has a cylindrically shaped hopper-like configuration. Consistent with this hopper-like configuration, receptacle 30 has a wide-mouth opening 31 at one end and a smaller aperture 32 opposite opening 31 at the other end of the receptacle. When inserted into container 22, separator assembly 25 is oriented so that larger opening 31 faces upwardly toward open end 28 and stopper 24, while aperture 32 is oriented to face downwardly or closed end 27. Preferably, opening 31 and aperture 32 are directly opposite each other and lie along a longitudinal axis inside the blood collection container. The outer diameter of cylindrically shaped receptacle 30 preferably is smaller than the inside diameter of blood collection container 22, as seen in FIG. 1, thereby providing an annular clearance 34 between receptacle 30 and inside wall 35 of the blood collection container. In order to maintain the separator assembly in position inside the collection container, a plurality of spaced ribs 36 is connected to the periphery of the receptacle and project outwardly therefrom. These ribs engage inside wall 35 of the container and, in the preferred embodiment, are slidable along the inside wall under the forces generated by centrifugation. It is appreciated that while four spaced ribs are illustrated and described, their number and illustrated configurations are not critical. These ribs not only provide the contact between separator assembly and blood collection container, but also provide the annular clearance between the receptacle and the inside wall of the container so that blood may pass therethrough toward the closed end of the container.

Deposited inside receptacle 30 is a barrier material 38. Under normal gravitational conditions (1-3g's) barrier material 38 has a consistency and viscosity which make it non-flowable; on the other hand, under increased gravitational forces, such as over 900g's and perhaps as high as 1,200g's minimally developed under standard centrifuge operations of the clinical laboratory type, barrier material 38 becomes flowable in the sense that its viscosity decreases as the applied g forces increase. Broadly speaking, this barrier material is thus designated as a thixotropic material inasmuch as these changing viscosity properties are demonstrated in this invention. As can be seen particularly in FIGS. 2 and 4, barrier material 38 is generally deposited into receptacle 30 through wide opening 31; under normal gravitational conditions, both the non-flow characteristics of the barrier material and the smaller size of aperture 32 cooperate to prevent the barrier material from flowing out of the aperture. Other properties of the barrier material are desirable as well and include the following: (1) that it not interact with the blood phases sought to be separated, and (2) that it be able to adhere to the inside wall of the container in order to provide a fixed barrier between the separated phases.

In all instances and embodiments of the present invention, barrier material 38 is selected to have a specific gravity intermediate the specific gravities of the lighter and heavier phases sought to be separated. For example, when whole blood is to be separated into serum and clotted blood, the serum phase normally has a specific gravity ranging between 1.002 and 1.040. Clotted blood on the other hand, is a heavier phase and normally has a specific gravity ranging between 1.070 and 1.090. Therefore, in this instance, the specific gravity of the barrier material will preferably lie between 1.040 and 1.050. With a specific gravity intermediate the specific gravities of the phases sought to be separated, the barrier material will form a layer at the interface between lighter and heavier phases of blood separated after the centrifuging operation. This process will be described more fully hereinafter.

Particularly when the separator assembly is slidable inside the blood collection container, it is preferable that the receptacle alone, i.e., including the spaced ribs, but excluding the barrier material therein, have a specific gravity greater than the heavier phase of blood sought to be separated. Therefore, and taking the example of blood being separated into serum and clotted phases, the specific gravity of the receptacle would normally have a range of 1.090 to 1.100. With this range of specific gravities, a receptacle would be forced toward the closed end of the container and thereby away from the interface between the separated phases of blood. It is only the barrier material which must travel to that interface, not the receptacle or the carrier for the barrier material. Therefore, by constructing the receptacle so that it has a specific gravity heavier than the heavier phase of separated blood, its function for carrying the barrier material will be satisfied as it moves away from the interface of separated phases toward the closed end of the blood collection container.

When the serum and clotted phases of blood are to be separated, it is desirable to include a blood clotting agent or activator inside the collection container so that blood may contact the activator and rapid clotting be induced. In the present invention, it is preferable to include a blood clotting activator 39 on the surfaces of separator assembly 25 which will be contacted by blood flowing into the collection container toward the closed end. As can be seen in FIGS. 1 and 2, clotting activator 39 is illustrated in the form of small particles adhered to the entire surface of separator assembly 25 to provide maximum surface area to increase the amount of clotting activator material available. While not limited thereto, clot activator 39 may be siliceous substances, such as glass, kaolin, bentonite, hydrated aluminum silicate and diatomaceous silica or the like substances which are well known in providing rapid coagulation of human blood. Such particles are described in U.S. Pat. No. 4,189,382. Such clot activating particles are deposited on the separator assembly and are removable therefrom when contacted by blood inasmuch as the blood flowing past would pick up these particles whereupon rapid coagulation would follow. It is appreciated that while the drawings herein illustrate the clot activating material as an element of the invention, inclusion of the clot activator with the invention is merely preferable, especially when the separating procedure involves serum and clotted blood. On the other hand, no clot activator is required if blood is intended to be separated into its cellular and plasma constituents. In this case, the separator assembly may be coated with heparin. As far as the amount of the barrier material to be included in the receptacle, there need only be enough to provide an effective physical layer at the interface between the separated phases while providing some adherence to the inside wall of the blood collection container. In a standard procedure for separating serum from clotted blood, the amount of barrier material may vary from approximately 1.0 cc to 3.5 cc, depending upon the overall size of the blood collection container and specimen collection volume.

Figure 5:
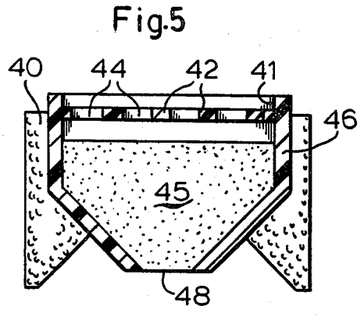
FIG. 5 is a cross-sectional view of an alternate embodiment of the separator assembly of the present invention.
Figure 6:
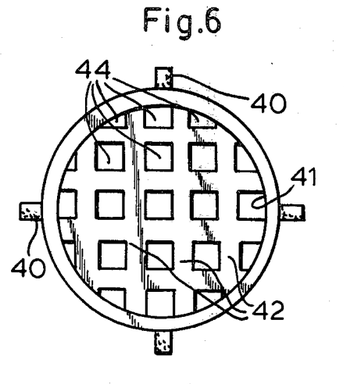
FIG. 6 is a top plan view of the separator assembly illustrated in FIG. 5.

While the embodiment of FIGS. 1-4 illustrate that the wide-mouth opening 31 is open or not covered, there are many variations which fall within the purview of the present invention. FIGS. 5-10 illustrate three such variations of the separator assembly. In FIGS. 5 and 6, separator assembly 40 is similar in all respects to separator assembly 25 except that its wider opening 41 includes a screen 42 with a plurality of small openings 44 to form an open mesh type of disk across opening 41. Screen 42 is positioned across opening 41 after barrier material 45 is placed inside receptacle 46. This screen operates to prevent flow of the barrier material out of opening 41 during centrifugation of the blood collection device. At the same time, screen 42 contributes to assure flow of the barrier material out of aperture 48 during the centrifuging operation.

Figures 7, 8:
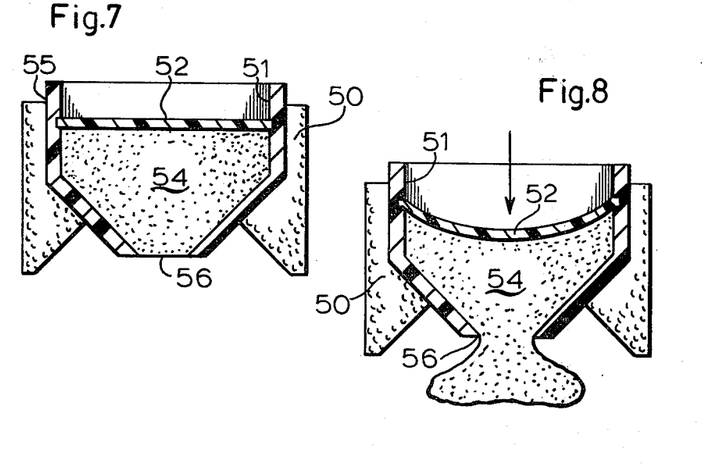
FIG. 7 is a cross-sectional view of another alternative embodiment of the separator assembly of the present invention illustrated under normal gravitational forces.
FIG. 8 is a cross-sectional view of the embodiment of FIG. 7 illustrating the separator assembly as it would appear during centrifugation.

In FIGS. 7 and 8, separator assembly 50 is similar in all respects to separator assembly 25 previously described, except that its wide opening 51 includes a flexible diaphragm 52 across the opening. This diaphragm is positioned across the opening after barrier material 54 is placed inside receptacle 55. Preferably, diaphragm 52 is adhered around its periphery to the inside of the receptacle wall at opening 51. During centrifugation, as illustrated in FIG. 8, flexible diaphragm 52 deflects under the forces developed by centrifugation and assists, primarily, in starting the actual flow of the barrier material out of aperture 56. This diaphragm may be made of rubber, plastic or other flexible materials compatible with the functions just described.

Figure 9:
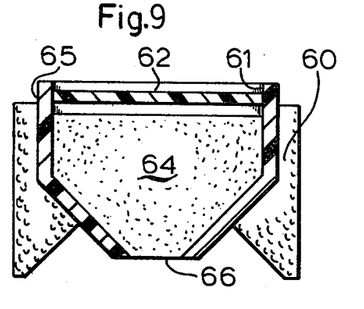
FIG. 9 is a cross-sectional view of another alternate embodiment of the separator assembly of the present invention illustrated under normal gravitational forces.
Figure 10:
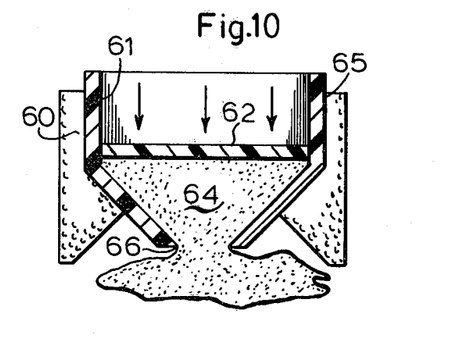
FIG. 10 is a cross-sectional view of the separator assembly of FIG. 9 illustrated as it would appear during centrifugation.

Turning to FIGS. 9 and 10, separator assembly 60 is also similar in all respects to separator assembly 25 previously described, except that its wider opening 61 includes a slidable piston 62 across that opening. Piston 62 is positioned across the opening after barrier material 64 is positioned inside receptacle 65. It is preferred that piston 62 have a specific gravity greater than a specific gravity of the ramainder of the separator assembly (absent the barrier material). This greater specific gravity of piston 62 will assure that the piston will move downwardly toward aperture 66 during centrifugation as seen in FIG. 10. In this fashion, piston 62 assists the flow of the barrier material through aperture 66 during centrifugation.

Figure 11:
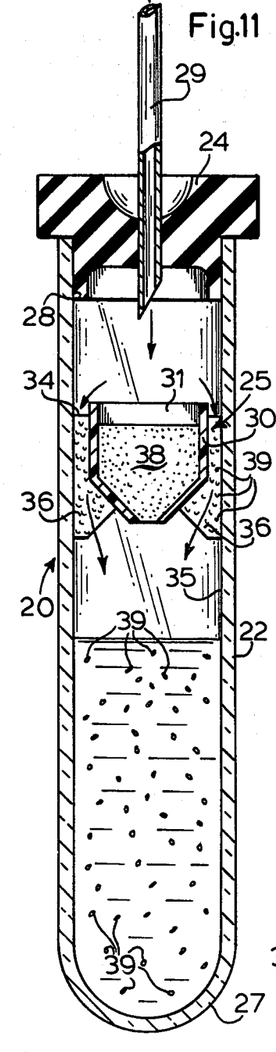
FIG. 11 is a cross-sectional view of the blood collection device taken along line 11—11 of FIG. 1 and illustrating a needle in position for delivering blood to the collection device before centrifugation.
Figure 12:
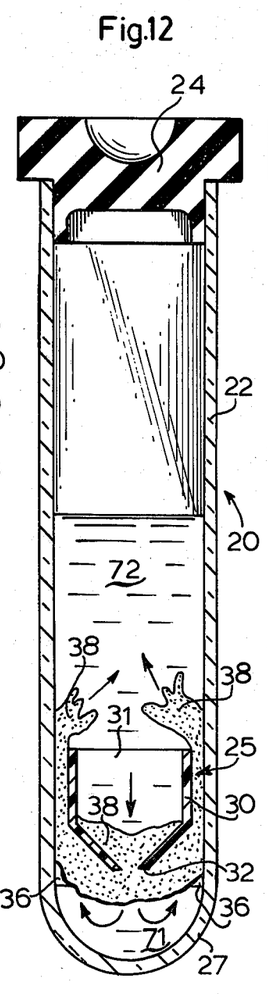
FIG. 12 is a cross-sectional view of the blood collection device of FIG. 11 illustrating the interior of the blood collection device at the early stages of centrifugation.

Referring now to FIG. 11, blood collection device 20 is illustrated during the blood collecting procedure with hollow needle 29 penetrating stopper 24 so that blood from the needle is directed into the interior of blood collection container 22. In the embodiment illustrated, separator assembly 25 includes clot activator material 39 in order to induce rapid clotting of blood which travels through passageway 34 between receptacle 30 and inside wall 35 of the collection container. Also, separator assembly 25 is positioned inside the evacuated container in a central region thereof intermediate closed end 27 and open end 28. As blood enters the interior of the collection container it travels through annular space 34 and contacts the peripheral surfaces of the separator assembly with the clot activator thereon. The blood washes the activator from those surfaces and picks up same as the blood travels toward closed end 27. As needle 29 is removed from the self-sealing stopper the blood at the closed end of the collection container is allowed to clot for the prescribed amount of time dependent upon the type of clotting activator. Once the blood has clotted the blood collection device is then centrifuged. FIG. 12 illustrates the blood collection device of FIG. 11 in the beginning stages of the centrifuging operation.

Figure 13:
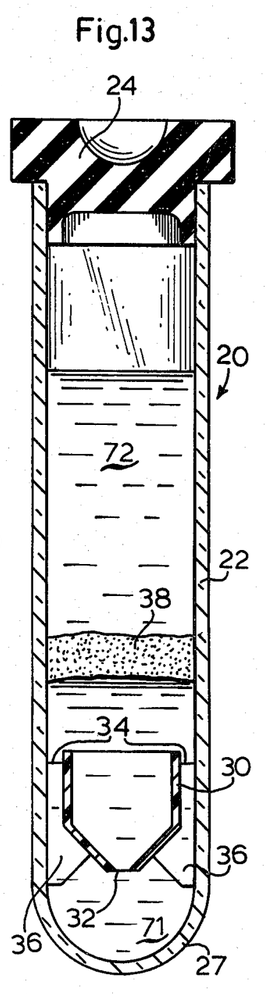
FIG. 13 is a cross-sectional view of the blood collection device of FIG. 11 after centrifugation is completed.

In the embodiment described in conjunction with FIGS. 11, 12 and 13, separator assembly 25 is positioned within container 22 so that it is slidable along inside wall 35 under the forces developed by centrifugation. In order to assure that separator assembly 25 slides downwardly or toward closed end 27 during centrifugation, the composite assembly, including receptacle 30, spaced ribs 36, activator material 39 (if any residual amounts have not been washed off) and barrier material 38 has a specific gravity greater than the specific gravity of the heavier phase of blood, in this case the clotted phase of blood. As mentioned earlier, the specific gravity of the receptacle alone (including spaced ribs and activator material) is also greater than the specific gravity of the heavier phase of blood to be separated. On the other hand, the specific gravity of barrier material 38 is intermediate the specific gravities of the lighter and heavier phases of blood to be separated.

During centrifugation as illustrated in FIG. 12, blood collection device 20 is oriented so that the centrifugal forces urge constituents therein with heavier specific gravity toward closed end 27 of the container. Forces of between 1,000 and 1,200g's typically are developed during the centrifuging operation. Under this level of force, the heavier, clotted phase of blood 71 separates from the lighter, serum phase of blood 72, with the heavier phase remaining at the closed end of the container while the lighter phase moves toward the stoppered end of the container. Under these same forces, separator assembly 25 slides downwardly inside container 22 toward the closed end since the specific gravity of the total assembly is greater than clotted phase 71. As soon as the separator assembly approaches the closed end, spaced ribs 36 become wedged at the point where the tube radius begins to form the closed end. Of course, for flat-bottom collection tubes (not shown), the bottom of ribs 36 will come to rest at the bottom of that type of tube. In either case, once the separator assembly comes to rest during centrifugation, barrier material 38, stressed beyond its yield point due to the centrifugal forces and its thixotropic properties, flows under its own influence during centrifugation through aperture 32 initially toward closed end 27 of the blood collection container. However, because the barrier material has a specific gravity intermediate the two separated phases of blood, it travels upwardly through annular space 34 between the receptacle and the inside wall of the container toward the interface of the separated serum and clotted phases. The position of the separator assembly 25 with respect to the inside wall of the container provides a directional control for the upward movement of the barrier material. Specifically, movement of the barrier material out of the receptacle is first upwardly along the inside wall of the blood collection container and then movement toward the center of the container once the serum/clot interface is reached by the barrier material. It is noted, especially by referring to FIG. 12, that the barrier material provides an "umbrella" effect over clotted phase 71 as it moves toward the interface of the separated phases.

When centrifugation is complete, as seen in FIG. 13, barrier material 38 forms a layer or barrier between clotted phase 71 and serum phase 72 of the blood. The barrier material adheres to inside wall 35 of the container and forms a barrier that effectively resists displacement under handling and transportation of the collection device from the centrifugation site to a different laboratory analysis site. It is also pointed out that the "umbrella" effect of the barrier material during centrifugation provides a barrier layer relatively clean or free of red blood cells entrapped in its upper surface (the surface in contact with serum phase 72). With barrier material 38 effectively maintaining the separation between the phases, the serum phase can conveniently be decanted by pouring since the barrier material will remain in place to prevent any cells from the clotted phase from escaping during the pouring step. Empty receptacle 30, of course, remains embedded within clotted phase 71 during the removal of the serum phase.

Figure 14:
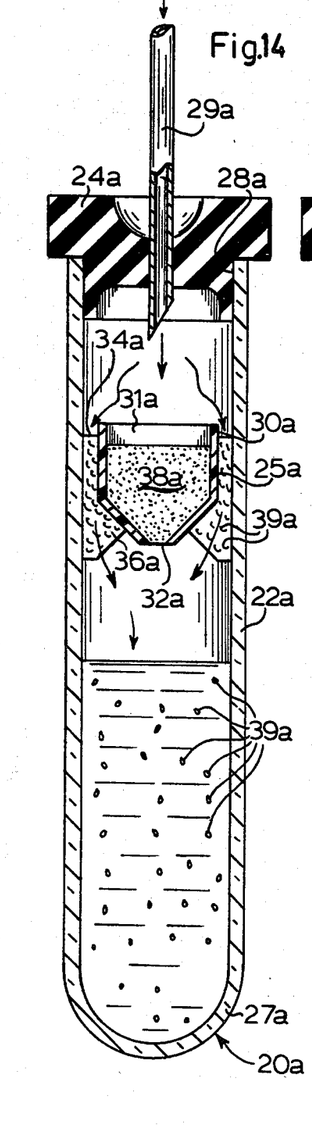
FIG. 14 is a cross-sectional view of a blood collection device including an alternate separator assembly therein having a specific gravity different from the separator assembly illustrated in FIG. 11.
Figure 15:
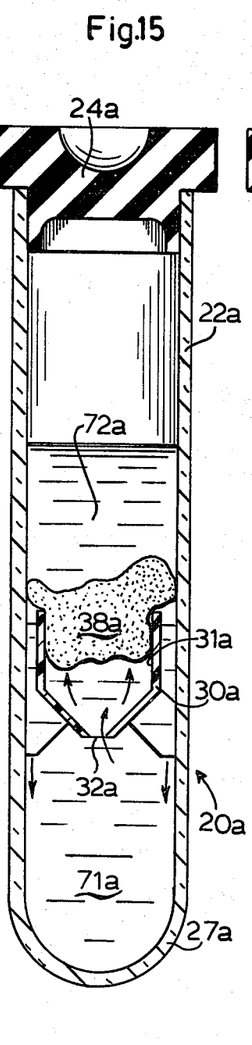
FIG. 15 is a cross-sectional view of the embodiment of FIG. 14 illustrating the blood collection device at the early stages of centrifugation after blood has been collected into the device.
Figure 16:
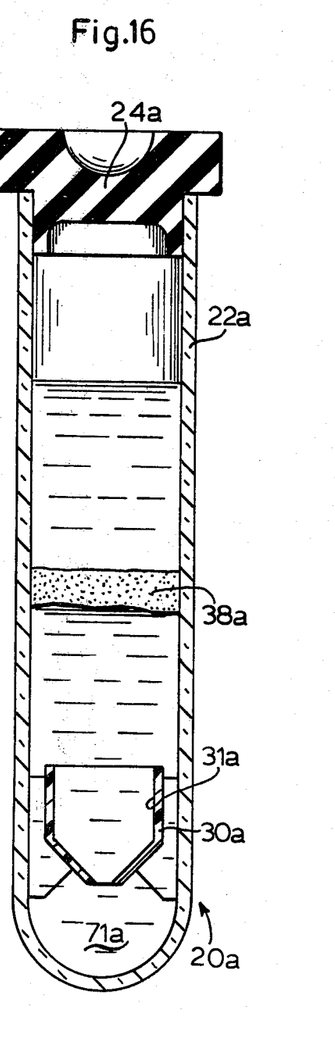
FIG. 16 is a cross-sectional view of the blood collection device of FIG. 14 illustrated after centrifugation has been completed.

FIGS. 14-16 illustrate an alternate embodiment of the separator assembly for use in a blood collection device. Separator assembly 25a, including barrier material 38a, is the same as the previously described separator assembly in all respects except one. Separator assembly 25a, as a composite unit including receptacle 30a, spaced ribs 36a, clot activator particles 39a and barrier material 38a, has a specific gravity intermediate the specific gravities of heavier, clotted blood phase and lighter, serum phase of blood. As in the previous embodiment, blood enters the evacuated blood collection container via hollow needle 29a, and picks up clot activator particles 39a as it travels through the annular passage 34a toward closed end 27a. After the blood has coagulated, the blood collection device is centrifuged as illustrated in FIG. 15.

During centrifugation, clotted phase 71a remains in the closed end of the container, while serum phase 72a is separated and moves toward the stoppered end of the container. Also, since both separator assembly 25a and barrier material 38a have a specific gravity intermediate that of the separated phases, the separator assembly slides downwardly toward the closed end until it reaches the interface between the separated phases. In this embodiment, as in the previous embodiment, the receptacle alone (including the spaced ribs and clot activator material which may be left thereon), has a specific gravity heavier than the heavier phase of blood. Therefore, the receptacle continues its downward movement toward closed end 27a of the container during centrifugation. Centrifugal forces are generated upwardly through aperture 32a against the barrier material inside the receptacle. Both these centrifugal forces through the aperture and the continued downward movement of the receptacle cause barrier material 38a to flow through wider opening 31a of the receptacle. The barrier material then flows to a position intermediate the serum and clotted phases of blood separated during centrifugation. As seen in FIG. 16, the barrier material is adhered to inside wall 35a of the collection container in a fashion similar to the embodiment previously described. Decanting of the serum phase is readily accomplished due to the maintenance of the barrier layer between the separated phases of blood. Also, empty receptacle 30a remains embedded in clotted phase 71a during the decanting or pouring of the serum phase.

It is preferred that the receptacle/rib structure of the separator assemblies described herein be made of plastic, such as polyethylene. The specific gravity of such plastic can be controlled during the formulation or fabrication of the receptacle so that a receptacle alone and the entire separator assembly can have the specific gravities as described above. With respect to the barrier material, various gels have been described which have the properties of the barrier material heretofore mentioned. For example, such gels or barrier materials are described in U.S. Pat. Nos. 3,957,654 and 3,852,194. The preferred barrier material, however, is a polyester base formulation, having a specific gravity ranging between 1.040 and 1.050, a viscosity range at normal gravitational conditions (between 1 and 3 g's) between 400,000 and 600,000 centipoises, while at gravitational forces of approximately 1,000 g's the barrier material yields in the configuration of the embodiment. The viscosity at elevated g forces becomes low enough for the material to flow, thus being able to adhere to the surface of a glass, plastic or like smooth-faced container.

Thus, the present invention provides an improved blood collection device in which a sample of whole blood is adapted to be centrifuged into lighter and heavier phases. A separator assembly includes a flowable barrier material which will form a barrier layer at the interface of the lighter and heavier phases of blood separated during centrifugation. As a result, pouring or decanting is made easier for the laboratory clinician; in addition, the barrier layer resists displacement under handling and transportation of the collection container from centrifugation site to another laboratory analysis site. Furthermore, the separator assembly of the present invention provides directional control of the flow movement of barrier material during centrifugation so that it travels to the interface of the separated phases to provide a clean barrier layer clearly defining the separated phases of blood.

What is claimed is:

1. A blood collection device for receiving a sample of whole blood adapted to be centrifuged into a phase of lighter specific gravity and a phase of heavier specific gravity comprising:

a collection container having an open end and a closed end;

a stopper in said open end sealing same closed and being penetrable by a needle for delivering blood to said container;

a separator assembly positioned inside said container intermediate said open and closed ends adapted to move along a longitudinal axis therein and including a receptacle with a thixotropic barrier material in said receptacle, said receptacle having an aperture facing said closed end of the container, the size of said aperture and the viscosity of said thixotropic barrier material cooperating to prevent said barrier material from flowing out of said aperture under normal gravity conditions; said separator assembly having a specific gravity greater than the specific gravity of the heavier blood phase and adapted to move toward said closed end during centrifugation of said device, said barrier material having a specific gravity intermediate the specific gravities of the lighter and heavier phases of blood and adapted to flow under its own influence through said aperture during centrifugation of said device, travel to a position intermediate the lighter and heavier phases of blood separated during centrifugation and adhere to the inside wall of said container to form a barrier between said phases to maintain the separation therebetween; and said receptacle having a smaller transverse dimension than the inside wall of said container to provide annular clearance therebetween for blood passage toward the closed end of said container during the blood collection procedure and for the passage of barrier material toward the interface of the phases separated during centrifugation.

2. The device of claim 1 wherein the interior of said container is evacuated.

3. The device of claim 1 wherein said receptacle alone has a specific gravity greater than the specific gravity of the heavier blood phase.

4. The device of claim 1 wherein said assembly further includes a plurality of circumferentially spaced ribs around said receptacle slidably engaging the inside wall of said container.

5. The device of claim 1 wherein said assembly further includes a removable blood clotting activator at least on its surfaces bordering the annular clearance so that whole blood contacting said activator during passage through said clearance picks up said activator and rapid blood clotting is induced.

6. The device of claim 5 wherein said activator is silica.

7. The device of claim 1 wherein said receptacle is made of plastic.

8. The device of claim 1 wherein said barrier material includes a polyester material.

9. The device of claim 1 wherein said receptacle has an access opening opposite said aperture for facilitating the deposit of barrier material into said receptacle.

10. The device of claim 1 wherein said receptacle further includes means across said access opening for preventing flow of the barrier material out of said access opening and assuring flow out of said aperture during centrifugation of said device.

11. The device of claim 10 wherein said means is an open mesh screen.

12. The device of claim 10 wherein said means is a flexible diaphragm.

13. The device of claim 10 wherein said means is a piston slidable toward said aperture to assist the flow of said barrier material through said aperture during centrifugation.

14. A blood collection device for receiving a sample of whole blood adapted to be centrifuged into a serum phase of lighter specific gravity and a clotted phase of heavier specific gravity comprising:

an elongate, evacuated collection container having an open end and a closed end;

a stopper in said open end sealing same closed and being penetrable by a needle for delivering blood to said container; and a separator assembly positioned inside said container intermediate said open and closed ends adapted to move along the longitudinal axis of said container and including a receptacle with a thixotropic barrier material therein, said receptacle having a smaller cross-sectional dimension than the inside wall of said container to provide an annular clearance therebetween for blood passage toward the closed end of said container during the blood collection procedure and to provide for the passage of barrier material toward the interface of the phases separated during centrifugation, said receptacle having a plurality of circumferentially spaced ribs around its periphery slidably engaging the inside wall of the container, said receptacle including an aperture facing said closed end of the container and an access opening opposite said aperture for facilitating the deposit of barrier material into said receptacle, the size of the aperture and the viscosity of the thixotropic barrier material cooperating to prevent said barrier material from flowing out of said aperture under normal gravitational conditions, said separator assembly including a removable blood clotting activator on its surfaces bordering the annular clearance so that whole blood contacting said activator during passage through said clearance picks up said activator and rapid blood clotting is induced, said separator assembly and said receptacle alone each having a specific gravity greater than the specific gravity of clotted blood, said assembly adapted to move toward said closed end during centrifugation of said device, said barrier material having a specific gravity intermediate the specific gravities of the serum and clotted phases of blood and adapted to flow under its own influence through said aperture during centrifugation of said device, travel to a position intermediate the serum and clotted phases of blood separated during centrifugation and adhere to the inside wall of said container to form a barrier between said phases to maintain the separation therebetween.

* * * * *